United States Patent [19]

Kiminkinen

[11] Patent Number: 4,624,565

[45] Date of Patent: Nov. 25, 1986

[54] DEVICE FOR GUIDING THE SAMPLE FLOW IN AN ANALYZER

[75] Inventor: Kauko E. Kiminkinen, Espoo, Finland

[73] Assignee: Outokumpu Oy, Espoo, Finland

[21] Appl. No.: 648,758

[22] Filed: Sep. 7, 1984

[30] Foreign Application Priority Data

Sep. 16, 1983 [FI] Finland ................................ 833321

[51] Int. Cl.[4] .......................... G01J 3/30; G01N 21/72
[52] U.S. Cl. ..................................................... 356/315
[58] Field of Search ................................ 356/315, 417

[56] References Cited

U.S. PATENT DOCUMENTS 3,516,771 6/1970 Rendina ........................ 365/315 X

FOREIGN PATENT DOCUMENTS 900123 1/1982 U.S.S.R. ............................... 356/315

*Primary Examiner*—Vincent P. McGraw
*Attorney, Agent, or Firm*—Dellet, Smith-Hill and Bedell

[57] ABSTRACT

The invention concerns a device for guiding the sample flow in an analyzer, especially in an atomic absorption spectrophotometer, in order to accomplish an essentially even flow front. Consistent with the invention, the burner (11) has been equipped with a flow divider (12) that due to its advantageously chosen construction and manufacturing material also works as a drop eliminator that removes the harmful drops, which are present in the sample spray.

8 Claims, 10 Drawing Figures

DEVICE FOR GUIDING THE SAMPLE FLOW IN AN ANALYZER

This invention concerns a device meant for guiding the sample flow in an analyzer, especially in an atomic absorption spectrophotometer, by placing a flow divider in the sample burner to accomplish an essentially even flow front.

Atomic absorption spectrophotometers are often equipped with a laminar flow burner in which the combustion gases, for example a mixture of air and acetylene, are mixed with the solution to be measured. The actual atomization of the elements to be measured takes place in the burner flame, whose properties are adjusted by the ratio of the combustion gases. The spraying of the sample must be as uniform as possible so that the amount of atoms produced in the flame would be constant and the distribution would be even throughout is length.

The disadvantage of the burners used nowadays is the uneven distribution of the sample spray inside the burner and from the burner through the port into the flame. The distribution of the burner gases is rather even due to their velocity, but most of the gas flows from the middle of the burner so that the temperature between different parts of the burner varies. Because of this the sample atomizes unevenly. Because the sample spray has slower mobility in respect with the gases, a large part of the sample spray is discharged from the middle of the burner thus preventing the even distribution of the sample throughout the whole area of the burner.

The quality of the sample spray is defined by the construction of the atomizer. The largest part of the sample spray cannot be utilized when using known device solutions, because the spray includes sample drops of different sizes, which condense into larger drops when colliding with the drop eliminator located in front of the atomizer. Some of the small drops, however, are conveyed into the burner together with the sample spray and from there on to the port. As this takes place the atomization of the sample is disturbed and the so called flame disturbance occurs, which in its turn results in a measuring breakdown. This is seen especially when measuring small concentrations. A drop in the burner, when it is conveyed to the flame, can result even in a shadow instead of absorption.

The purpose of the invention being presented is to remove some of the disadvantages of the prior art and to accomplish a device, with which the analyzer sample flow is guided in the burner essentially connected with the analyzer in order to establish an essentially even homogenous flow front.

The essential characteristics of the invention are set forth in the patent claim 1.

According to the invention the gases and the sample spray are led past an advantageously shaped flow divider in the atomic absorption spectrophotometer, and the combustion gases and the sample spray are distributed evenly through the whole area of the burner port. If some drops are now conveyed in the sample spray, they disintegrate on colliding with the divider that is advantageously at essentially the same temperature and thus the drops do not cause any flame disturbance. The divider promotes the formation of flow resistance between the actual mixing chamber and the burner, which on its part improves the stability and miscibility of the combustion gases and sample spray.

In the following the invention is described in reference with the drawings enclosed, in which FIG. 1 shows schematically a side view of a prior art laminar flow burner with its mixing chamber used in an atomic absorption spectrophotometer.

Figure 2:
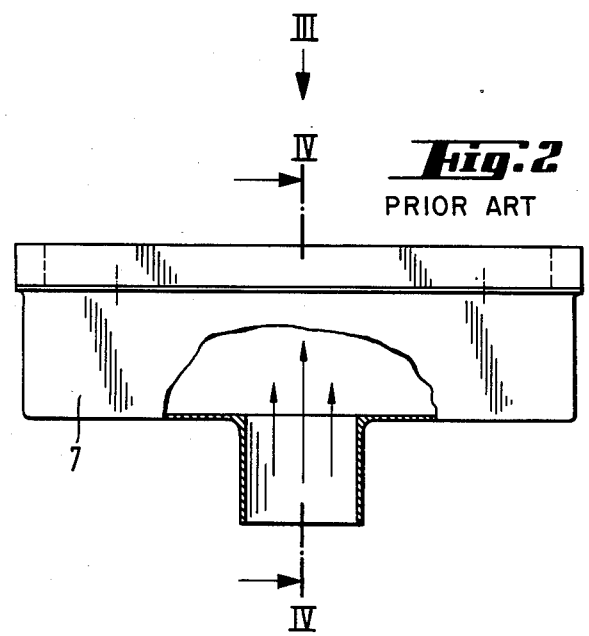
FIG. 2 is an enlarged side view of the burner shown in FIG. 1.
Figure 4:
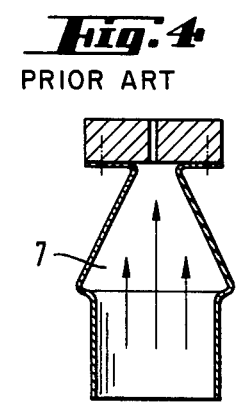
Figure 3:
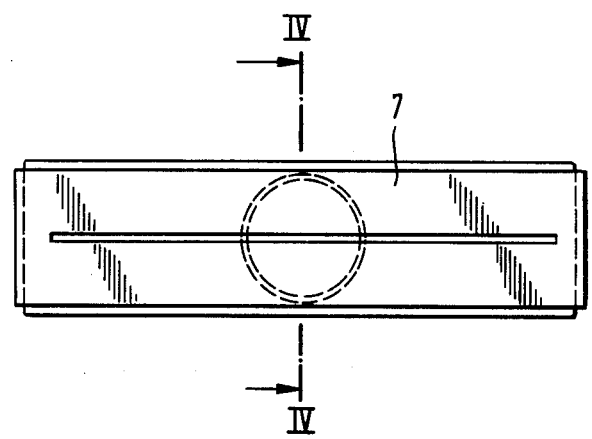
FIG. 3 shows the device of FIG. 2 seen in the direction of the arrow-III.
Figure 5:
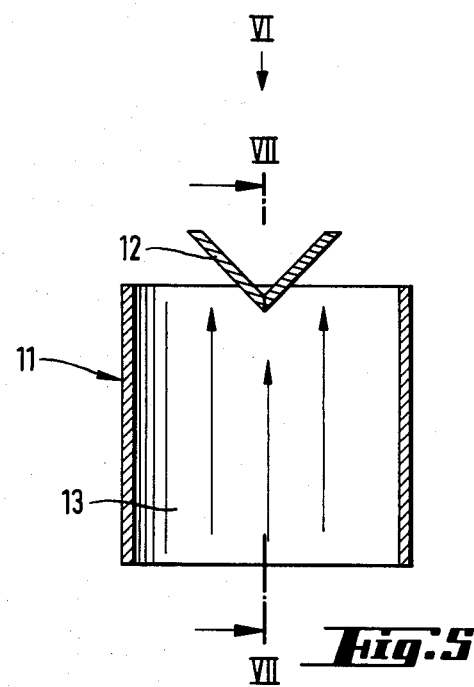
Figure 7:
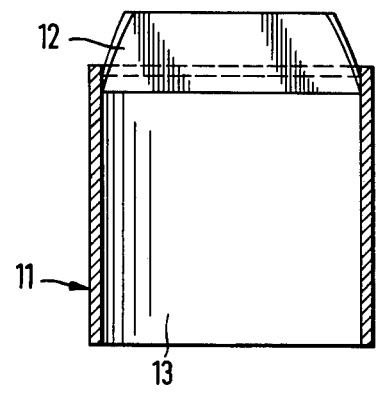
Figure 6:
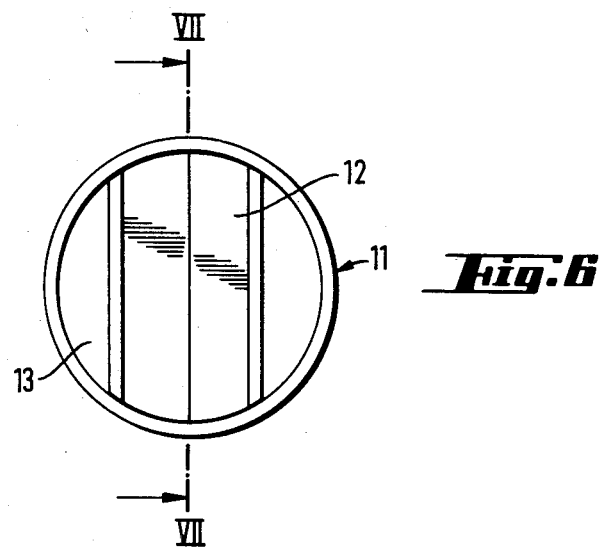
Figure 8:
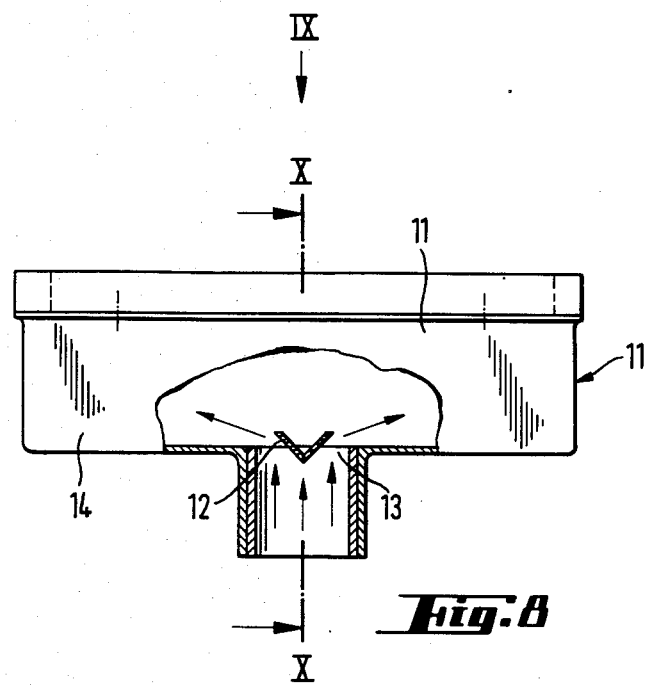
Figure 10:
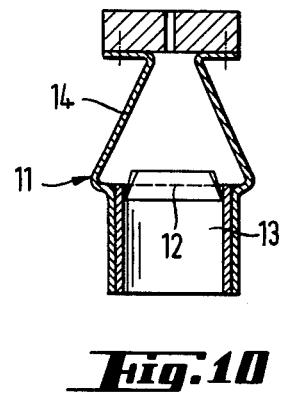
Figure 9:
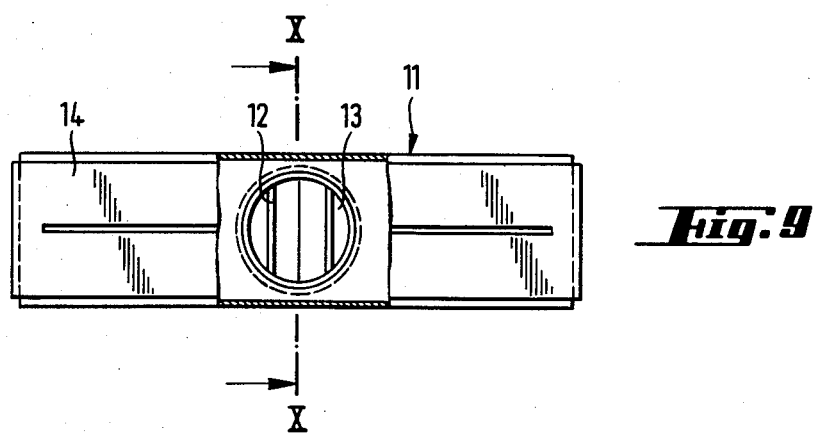

FIG. 4 is a cross-section of the device of FIGS. 2 and 3 taken along the line IV—IV, FIG. 5 shows schematically the cross-section of a component of a burner device embodying the invention FIG. 6 shows the device of the FIG. 5 seen in the direction of the arrow VI, FIG. 7 shows a cross-section taken along line VII—VII in FIG. 5, FIG. 8 shows the device of FIG. 5 placed in a prior art burner for an atomic absorption spectrometer, FIG. 9, shows partially cut away the device of the FIG. 8 seen in the direction of the arrow IX, and FIG. 10 shows a cross-section of the device of FIG. 8 taken along line X—X in FIGS. 8 and 9.

Figure 1:
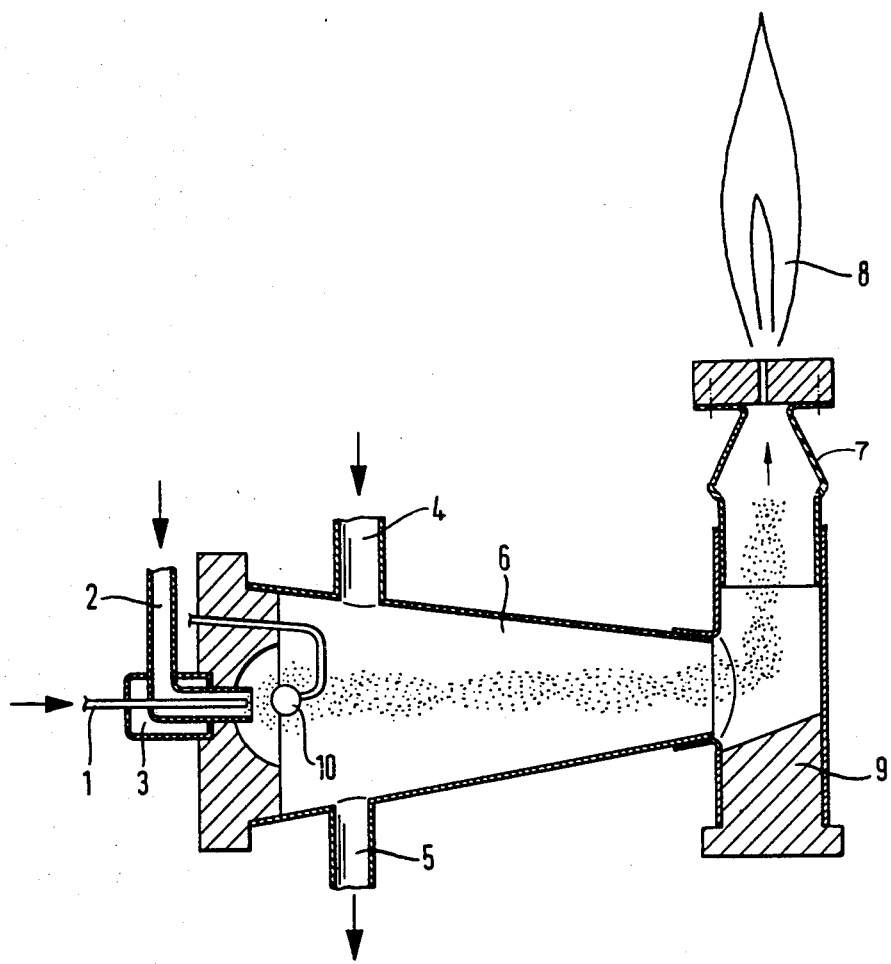

According to FIG. 1 the sample 1 and compressed air 2 are fed through the atomizing part 3 into the mixing or atomizing chamber 6, where the acetylene 4 is also led. A drop eliminator 10 is placed also in front of the sample 1 entrance port. The drop eliminator removes most of the drops, which are drained from the atomizing chamber 6 through the discharge port 5. The conical shape of the mixing chamber 6 promotes also the draining of sample drops. The sample flow to be analyzed is conveyed together with the combustion gases (air and acetylene) from the atomizing chamber 6 to the burner 7, where the flame 8 to be inspected is formed. A safety valve 9 for maintenance and repair work has been placed on the opposite side of the burner 7 in the same mixing chamber 6.

A prior art burner 7 is shown in FIG. 2 from the side and in FIG. 3 from above. In FIG. 4 the burner is seen in cross-section taken along the line IV—IV shown in FIGS. 2 and 3. The arrows drawn in FIGS. 2 and 4 present schematically the sample spray flow. Due to the slower mobility of the sample spray than the gases a large part of the sample spray is discharged outwards from the middle of the burner 7. The burner 11, according to the invention and shown in FIG. 5, is so designed that it can replace the prior art burner 7 in the device shown in FIG. 1. In the burner 11 the gases 2,4 are led past an essentially V-shape, transversely mounted flow divider 12, which is manufactured from proper material such as titanium. In FIGS. 5-7 and 8-10, in which the burner 11 embodying the invention is placed in a prior art atomic absorption spectrophotometer, the burner 11 is shown both from the side, FIGS. 5 and 8, and from above, FIGS. 6 and 9. In addition to this, the cross-section VII—VII in FIGS. 5 and 6 is shown in FIG. 7, and, correspondingly, the section X—X in FIGS. 8 and 9 is shown in FIG. 10. According to FIGS. 5 to 10, the combustion gases 2,4 and the sample spray are led into the burner 11 and there from past the flow divider 12 placed tranversely in the port 13 through the burner ends 14. The combustion gases 2,4 and the sample spray are thus distributed evenly throughout the whole area of the port 13, as described with the arrows in FIGS. 5 and 8.

At the same time as the flow divider 12 situated in the burner 11, embodying the invention, accomplishes the balancing of the flow front, the divider 12 can also be used as an eliminator of the drops coming with the sample spray. When the divider 12 is manufactured from advantageously thermopositive material, i.e. material of high thermal conductivity the divider is made to heat up to the same temperature as the burner 11 and the drops arriving at the divider 12 with the sample spray disintegrate and thus do not cause a flame disturbance in the flame being analyzed. A large part of the sample spray entering the mixing chamber 6 can now also be used advantageously in analyzing and a special drop eliminator 10 is not necessarily needed in the mixing chamber 6.

Even though the divider 12 has been mentioned before as essentially V-shaped, the planes in the divider 12 can intersect in different angles between 30°–120°, depending on flow conditions. In addition, the shape of the divider 12 does not have to be that of two intersecting planes, but it can also be e.g. cup-shaped of even a combination of these two shapes. The most important point in selecting the shape is to accomplish a divider 12, with which even flow conditions are obtained in the burner 11 in order to establish a reliable analysis result and with which it is easy to eliminate the drops in the sample spray, which would otherwise disturb the analysis.

The material of the divider 12 must be chosen so that it withstands dissolving acid such as hydrochloric acid and sulphuric acid, which occur frequently in the sample solution. The material is also required to have a comparatively good heat conductivity in order to reach essentially the same temperature as the burner 11 and remove the harmful drops present in the sample spray.

I claim:

1. A burner device for a flame reaction analyzer, comprising wall means defining at least one inlet port for combustion gas, a burner outlet port, and a passageway for conducting a flow of combustion gas from the inlet port to the burner outlet port, and the device also comprising means for introducing material to be analyzed into the flow of combustion gas, and a flow divider located in said passageway at a position upstream, with respect to the flow of combustion gas, of the burner outlet port and downstream of said means for introducing material, said flow divider comprising two substantially planar elements connected together in a V-shape with the point of the V directed away from the burner whereby the flow divider is concave towards the burner.

2. A device according to claim 1, wherein the passageway from the inlet port to the burner outlet port includes an elongate horizontal portion and an elongate vertical portion, each portion having first and second ends, the gas inlet port being located at said first end of the horizontal portion and the vertical portion being connected at its first end to the second end of the horizontal portion, the burner outlet port being at the second end of the vertical portion and the flow divider being located in said vertical portion.

3. A device according to claim 1, wherein the angle of intersection between the two planar elements is in the range from 30 degrees to 120 degrees.

4. A device according to claim 1, wherein the flow divider is formed from material that is corrosion resistant and is a good thermal conductor.

5. A device according to claim 1, wherein the flow divider is made of titanium.

6. A burner device for a flame reaction analyzer, comprising wall means defining at least one inlet port for combustion gas, a burner outlet chamber, an elongate burner outlet port opening from the burner outlet chamber, and a passageway for conducting a flow of combustion gas from the outlet port and opening into the burner outlet chamber, the burner outlet chamber being substantially rectangular in section and the opening from the passageway into the burner outlet chamber having a linear dimension parallel to the longer dimension of the rectangular section of the burner outlet chamber that is substantially smaller than said longer dimension, and the device also comprising means for introducing material to be analyzed into the flow of combustion gas, and a flow divider located substantially at the position of said opening and extending in a direction substantially perpendicular to the long dimension of the rectangular section of the burner outlet chamber.

7. A burner device according to claim 6, wherein the flow divider is substantially V-shaped in cross section with the point of the V directed away from the burner outlet chamber.

8. A burner device according to claim 7, wherein the flow divider comprises two substantially planar elements that are connected together in a V-shape, the angle of intersection between the two planar elements being in the range from 30 degrees to 120 degrees.

* * * * *